United States Patent [19]

Chapman et al.

[11] Patent Number: 5,360,734
[45] Date of Patent: Nov. 1, 1994

[54] METHOD FOR INACTIVATING PATHOGENS IN ERYTHROCYTES USING PHOTOACTIVE COMPOUNDS AND PLASMA PROTEIN REDUCTION

[75] Inventors: John Chapman, Lake Villa, Ill.; Patricia M. Logan; Herma C. Neyndorff, both of Vancouver British Columbia, Canada; Janice North, Vancouver British Columbia, Canada

[73] Assignees: Baxter International, Inc., Deerfield, Ill.; Quadra Logic Technologies, Inc., Vancouver British Columbia, Canada

[21] Appl. No.: 10,469

[22] Filed: Jan. 28, 1993

Related U.S. Application Data

[63] Continuation of Ser. No. 718,747, Jun. 21, 1991, abandoned.

[51] Int. Cl.$^5$ ............................ C12N 7/06; A01N 1/02
[52] U.S. Cl. .................................. 435/238; 435/2
[58] Field of Search ................................ 435/2, 238

[56] References Cited

U.S. PATENT DOCUMENTS

| | | | |
|---|---|---|---|
| 4,775,625 | 10/1988 | Sieber | 435/238 |
| 5,091,385 | 2/1992 | Gulliya et al. | 514/224.8 |
| 5,120,649 | 6/1992 | Horowitz et al. | 435/173 |

FOREIGN PATENT DOCUMENTS

| | | |
|---|---|---|
| 0457196 A2 | 5/1919 | European Pat. Off. |
| 0184331 | 11/1985 | European Pat. Off. |
| 0196515 | 3/1986 | European Pat. Off. |

WO88/1087 12/1988 WIPO.

OTHER PUBLICATIONS

Dodd, R. Y. et al., Transfusion 31:483–490 (1991).
Feix, J. B. et al., BBA 1075:28–35 (1991).
Wagner et al., Photochem Photo Biol 53:54S (1991).
Prodoux, K. N. et al, Transfusion 31:415–422 (1991).
Scott, J. et al, J. Photochem. Photo Biol B Biol 7:149–158 (1990).
De Paolis et al, Biochem. J. 226:757–766 (1985).
Moroff G, et al, Transfusion 29 (75) S15 (1989).
Cole M et al, transfusion 29(7S) S145 (1989).
H. C. Neyndorff et al, "Development of a Model to Demonstrate Photo–sensitizer–Mediated Viral Inactivation in Blood", Transfusion, vol. 30, No. 6, 1990, pp. 485–490.

*Primary Examiner*—Douglas W. Robinson
*Assistant Examiner*—Sandra Saucier
*Attorney, Agent, or Firm*—Hill, Steadman & Simpson

[57] ABSTRACT

The present invention provides a method for inactivating pathogens in a body fluid, such as plasma, red cells, platelets, leukocytes, and bone marrow. The present invention minimizes adverse effects caused by the photosensitive agents while retaining the disinfecting activity of such agents and processes. Pursuant to the present invention, prior to irradiating a body fluid including a photoactive drug, the extracellular fluid, which in the case of blood components includes plasma proteins is at least substantially reduced. Additionally, after the irradiation process, the resultant body fluid is prevented from contacting additional extracellular fluid, e.g., plasma proteins, for a predefined period.

34 Claims, 4 Drawing Sheets

| | MIN | MAX | COUNT | PERCENT | MEAN | SD | %HPCV |
|---|---|---|---|---|---|---|---|
| 1 | 1.416 | 6.410 | 6370 | 65.1 | 2.603 | 1.435 | 42.5 |
| 2 | 6.415 | 33.24 | 65 | 0.7 | 7.881 | 1.377 | 43.0 |
| 3 | 18.37 | 76.74 | 3 | 0.0 | 23.64 | 1.19 | 8.38 |
| 4 | 1.052 | 72.71 | 9777 | 100.0 | 1.959 | 1.692 | 57.8 |

FIG. 3b

| | MIN | MAX | COUNT | PERCENT | MEAN | SD | %HPCV |
|---|---|---|---|---|---|---|---|
| 1 | 1.416 | 6.41 | 645 | 7.0 | 4.114 | 1.484 | 41.0 |
| 2 | 5.916 | 33.24 | 8580 | 93.0 | 13.75 | 1.43 | 11.8 |
| 3 | 18.37 | 76.74 | 1875 | 28.3 | 21.52 | 1.18 | 12.6 |
| 4 | 1.052 | 72.71 | 9225 | 100.0 | 12.56 | 1.69 | 11.8 |

METHOD FOR INACTIVATING PATHOGENS IN ERYTHROCYTES USING PHOTOACTIVE COMPOUNDS AND PLASMA PROTEIN REDUCTION

This application is a continuation of application Ser. No. 07/718,747, filed Jun. 21, 1991, now abandoned.

BACKGROUND OF THE INVENTION

The present invention relates generally to a method for inactivating pathogens that may be contained in a body fluid. More specifically, the present invention relates to the inactivation of pathogens, especially in blood products, that can cause an infectious disease.

In a variety of therapies, such as transfusion and transplants, body fluids, especially blood components, such as red blood cells, platelets, plasma, leukocytes, and bone marrow, are infused from one or more individuals into a patient. Although such therapies provide treatments, some of which are life saving, and cannot otherwise be provided, due to the transmission of infectious diseases there may be potential risks to such therapies.

For example, it is known that blood can carry infectious agents such as hepatitis viruses, human immunodeficiency viruses (an etiological agent of AIDS) and herpes virus. Although screening methods exist to identify blood that may include such viruses, blood containing viruses, and other disease causing pathogens, such as bacteria, cannot be 100% eliminated from the pool of possible blood component supplies; there is still a small chance that blood transfusions can transmit viral infection. Accordingly, a goal of biomedical research has been to reduce the risk of transmitting an infectious agent by selectively inactivating or depleting pathogens present in such blood components.

One approach has been to utilize photosensitive (photoactive) agents that when activated by light of the appropriate wavelength will destroy the ability of the pathogen to cause infection. The use of photodynamic therapy has been suggested as a way to eradicate infectious agents from collected blood and its components prior to storage and transfusion. See, Neyndorff, et al, "Development of a Model to Demonstrate Photosensitizer Mediated Viral Inactivation in Blood", *Transfusion* 1990: 30:485–490; North et al, "Photodynamic Inactivation of Retrovirus by Benzoporphyrin Derivative: A Feline Leukemia Virus Model", Submitted to *Transfusion*; and Matthews et al, "Photodynamic Therapy of Vital Contaminants With Potential for Blood Bank Applications", *Transfusion*, 28(1), pp. 81-83 (1988).

Although effective in the destruction of the pathogen, photochemical inactivation of pathogens can also result in adverse effects on the therapeutic elements of the product, such as red blood cells or platelets. In this regard, it has been observed through immunohematology studies, that cells of blood components treated with photoactive agents which act on membranes have IgG and other plasma proteins associated with the cell membrane. IgG is an immunoglobulin plasma protein that when present is caused to bind with the cells during the photoactivation process.

Recent attempts to avoid this phenomenon have been unsuccessful. Wagner, et al., "Red Cell Surface Alterations Resulting From Virucidal Photochemical Treatment", Photochemistry & Photobiology 53: 54S, 1991, reports that "[u]nexpectedly, agglutination tests using rabbit anti-human IgG on [methylene blue] or [merocyanine 540] phototreated cells indicated that photosensitized red-cells have IgG associated with their surface. Plasma depletion by washing red cells prior to phototreatment did not prevent this IgG binding upon subsequent addition of untreated autologous or AB plasma."

The presence of IgG bound to the membrane of red cells raises a host of potential concerns and difficulties in using photoinactivation drugs to inactivate pathogens in blood components. Physiological issues include reticuloendothelial system clearance of the treated red cells and complement activation. Red cells coated with IgG may be removed too quickly in a transfusion patient by the RES system.

Perhaps as important a concern with respect to IgG binding, even if the presence of IgG has no effect on cell survival or product safety, is with respect to the diagnostic implications. After treatment, the IgG bound to the cells cannot be removed from the cell membranes by washing the cells; even if extensive washings are performed. Because of the binding of the IgG to the cells, the cells exhibit a positive test result when direct antiglobulin test (DAT or Coombs') is employed.

The Coombs' test is used to detect antibody on red blood cells. The test uses rabbit antisera to immunoglobulin. When cells coated with IgG are mixed with the rabbit antisera, agglutination occurs. If IgG coated red cells are transfused into a patient, a physician loses one of his important diagnostic tests in understanding hematologic changes in the patient, since all patients receiving such a product will exhibit a positive Coombs' test.

The use of such IgG coated cells would prevent many of the currently used serological and diagnostic testing procedures. For example, red cells are typically screened using the Coombs' test. Accordingly, although the photoactive agents can result in a reduction of viable pathogens, the resulting disadvantages inherent in IgG bound red cells may outweigh the advantages.

Further, any commercially viable process for inactivating pathogens must have an activation phase that does not have an undue duration. The photoactivation phase of such photodynamic processes is dependent on the amount of photoactive agent present. However, initially the body fluid must be loaded with a sufficient amount of photoactive agent to insure that all of the pathogens bind with the agent. Therefore, excess photoactive agent could increase the activation phase of the process.

SUMMARY OF THE INVENTION

The present invention provides a method for inactivating pathogens in a body fluid, such as red cells, platelets, leukocytes, and bone marrow. The present invention minimizes adverse effects caused by the photosensitive agents while retaining the disinfecting activity of such agents and processes. To this end, at least 5-6 logs of viruses are inactivated in a red cell unit with less than 2% hemolysis over a fourteen (14) day storage period pursuant to an embodiment of the present invention. The procedure results in the killing of pathogenic contaminants, such as viruses. The normal cells, or tissues, maintain their functional integrity and in the case of red cells, do not exhibit a positive direct antiglobulin test.

Pursuant to the present invention, a method for destroying pathogens in a fluid containing cells prepared for medical use is provided comprising the steps of treating the cells in the presence of a photoactive agent under conditions that effect the destruction of the pathogen, the treatment step being performed in a fluid having a reduced content of extracellular protein and additionally, after the irradiation process, the resultant body fluid is not allowed to contact such extracellular protein, e.g., plasma proteins, for a predefined period.

It has been found, with respect to red cells, that after activation of the photoactive agent that at least some of the red cells have a nonspecific affinity for plasma proteins. If the irradiated red cells are combined with plasma proteins, either in vivo or in vitro, within a certain time period after the irradiation process they will bind with at least the IgG proteins present in the plasma. However, if one waits a predetermined time period, the red cells will not significantly bind with plasma proteins including IgG. It has been found with respect to benzoporphyrin derivatives that a waiting period of at least approximately three (3) hours is sufficient. In an embodiment, the preferred waiting period is approximately eighteen (18) hours.

The extracellular fluid can be removed from the body fluid through washing, filtration, or other methods, either prior to or after the photoactive agent is added to the body fluid.

In an embodiment, the present invention provides a method for inactivating pathogens in a body fluid comprising the steps of: adding a photoactive agent to a collected body fluid; treating the body fluid to remove, or at least substantially reduce, the unbound photoactive agent and the extra-cellular components; and irradiating a resultant body fluid with an appropriate light to inactivate pathogens in the resultant body fluid.

In an embodiment, a method for inactivating a pathogen in a blood component is provided comprising the steps of: adding a photoactive agent to a collected blood component; allowing the photoactive agent to equilibrate with the blood component; treating the blood component to substantially reduce or remove unbound photoactive agent and plasma protein; irradiating a resultant blood component with light of an appropriate wavelength to inactivate pathogens; and waiting at least approximately three (3) hours before allowing the resultant blood component to contact plasma and/or other protein containing material.

In an embodiment, a method is provided for inactivating a pathogen in a blood component including red cells comprising the steps of: treating a blood component to reduce the plasma proteins; adding a photoactive agent to the blood component; irradiating a resultant blood component with light of appropriate wavelength to inactivate pathogens; and preventing the irradiated blood component from contacting a protein containing composition for a predetermined period.

Preferably, pursuant to the present invention, not more than approximately 5% by weight of the total weight of the blood component comprises plasma proteins remain after the treating steps.

In an embodiment of the present invention, the photoactive agent is chosen from the group including, but not limited to: porphyrins; porphyrin derivatives; merocyanines, such as MC540; phthalocyanines, such as aluminum phthalocyanine, other pyrrolic macrocycles; psoralens; and other photoactive dye stuffs, such as methylene blue. In a preferred embodiment, the photoactive drug is a benzoporphyrin derivative.

In an embodiment, the step of allowing a photoactive drug to equilibrate has a duration of approximately 5 minutes to about 6 hours.

In an embodiment, the treating step includes a washing step comprising: centrifuging the blood component product to form a pellet; removing the supernatant; and resuspending the pellet.

In an embodiment, the treating step includes a filtration step.

If desired, a plurality of washing steps can be utilized in the method of the present invention.

In an embodiment, a storage solution is added to the irradiated resultant product.

In an embodiment after at least a three (3) hour period the blood component is infused into a patient.

Additional features and advantages of the present invention are described in, and will be apparent from, the detailed description of the presently preferred embodiments and from the drawing.

DETAILED DESCRIPTION OF THE PRESENTLY PREFERRED EMBODIMENTS

The present invention provides a method for inactivating pathogens in a body fluid. Specifically, the present invention is directed to a method for inactivating pathogens such as viruses that cause the transmission of infectious disease, from blood and blood component supplies.

As used herein, the term "body fluid(s)" includes blood components such as, plasma or plasma components, red cells, leukocytes, and platelets, bone marrow, cells generated in tissue cultures, and semen. However, reference in the instant patent application, by way of example, is made to blood components and specifically red cells.

Generally, the method of the present invention inactivates pathogens by adding a photoactive agent to the body fluid and activating the photoactive agent to inactivate the pathogen. With respect especially to blood components, prior to either the addition of the photoactive agent or irradiation of same, plasma proteins, such as IgG, are removed or substantially reduced. After the irradiation step of the method, the blood component is not infused into a patient or combined with plasma and/or other protein containing material until after the expiration of a predefined time period.

It is believed, at least with respect to BPDs, that this time period should be at least approximately three (3) hours and preferably approximately eighteen (18) hours. The time period may be different depending on the photoactive agent that is utilized. What is critical is that there is some time delay between photoactivation and plasma protein contact.

The present invention provides many advantages including an increased "therapeutic window" for treatment. The method results in increased viral inactivation and/or depletion.

It has also been found that with respect to red cells, the method results in increased stability of the red cells on storage compared to those cells wherein a photoactive agent is activated in the presence of plasma proteins. Additionally, the method eliminates the previous problems of direct antiglobulin test (DAT) positivity.

Further, smaller quantities of photosensitizer (BPD) are required to achieve maximum (up to 100%) vital inactivation and/or depletion. Likewise, in an embodiment of the invention, decreased amounts of photosensitizers and/or photoproducts are present in final product by using a washing step carried out following incubation with photosensitizer and immediately before light exposure.

In an embodiment, the method comprises the steps of adding a photoactive agent to a collected body fluid, such as a blood component. The photoactive agent is allowed to equilibrate with the body fluid. The body fluid is then treated through washing or some other step to remove, or at least substantially reduce, unbound photoactive agents and extra-cellular material, e.g. plasma and proteins. The resultant body fluid is then irradiated with an appropriate light to inactive pathogens in the resultant body fluid.

A number of photoactive agents have been identified that have membrane activity and can, when irradiated, inactivate pathogens, such as viral agents, in the blood. These photoactive agents include porphyrins, porphyrin derivatives, merocyanines such as MC 540, phthalocyanines such as aluminum phthalocyanine, other pyrrolic macrocycles, psoralens, and photoactive dye stuffs such as methylene blue. As previously noted, at least some of these photoactive agents can also exhibit certain disadvantages when used with at least some body fluids, such as red blood cells. The present invention avoids these disadvantages while maintaining the advantageous effects of these agents.

Photoactive compounds include, by way of example, a family of light-activated drugs derived from benzoporphyrin. These derivatives are commonly referred as BPDs. BPDs are available from Quadra Logic Technologies, Inc., Vancouver B.C., Canada.

BPDs, similar to other types of hematoporphyrin derivatives, have an affinity for the cell walls or membranes of many viral organisms that are carried in blood. They therefore bind or attach themselves to the cell walls or membranes. When exposed to radiation, BPDs undergo an energy transfer process with oxygen, forming singlet oxygen. When the singlet oxygen oxidizes, it kills the biological cells to which it has attached. Other photochemical events may contribute to cell killing.

It has been found that when at least a blood component is used, the plasma proteins must be eliminated, or at least substantially reduced, prior to irradiation of the photoactive agent. The elimination, or substantial reduction, of the plasma proteins can occur either prior to adding the photoactive agent to the blood component or after it is added. As discussed in detail hereinafter, certain additional advantages are achieved depending on when the removal step occurs. Regardless, as also set forth in detail below, a critical step is that after the irradiation process, the blood component is prevented from contacting, either in vivo or in vitro, additional plasma proteins for a predefined time period. It is believed, at least with respect to BPDs, that this time period should be at least approximately three (3) hours after irradiation.

Pursuant to an embodiment of the present invention, first the photoactive agent is added to the component fluid, for example, red blood cells. The photoactive agent is allowed to equilibrate with the fluid, e.g., red cells. As used herein, "equilibrate" means that the agent is distributed to the different compartments of the fluid. However, equilibrate does not mean that equilibrium is necessarily achieved.

Figure 1:
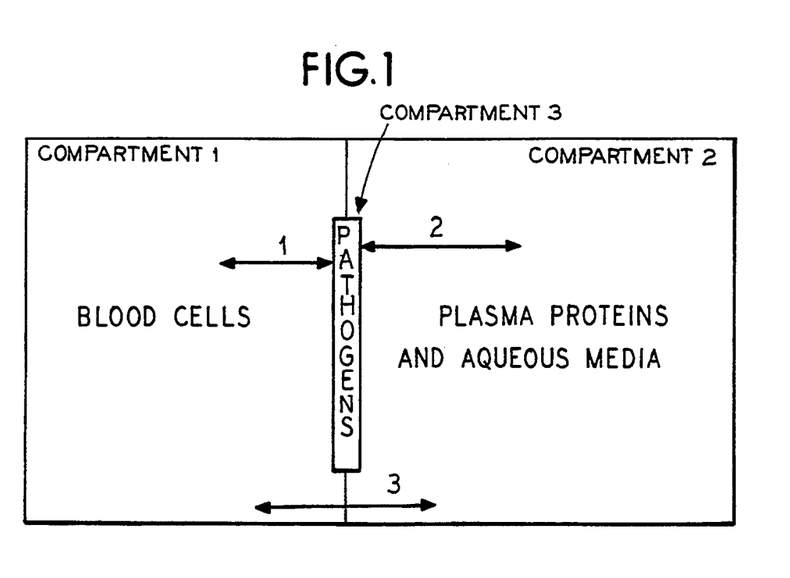
FIG. 1 illustrates conceptually a three compartment model for the distribution of a photosensitive drug when added to an unwashed blood component.

Referring to FIG. 1, in the model illustrated, the blood component comprises three compartments: blood cells; pathogens; and plasma proteins and aqueous media (extra-cellular fluid). FIG. 1 illustrates the equilibrated state with respect to: the blood cells and pathogens; the plasma proteins and pathogens; and the plasma proteins and blood cells. The equilibrated state is important to insure that all, if not a substantial portion, of the pathogens will be inactivated.

Applicants have found that preferably the time required after the photoactive agent is added to the fluid to reach the equilibrated stage is approximately five (5) minutes to about six (6) hours. Within five (5) minutes it is believed that sufficient agent is distributed to the pathogen compartment. Applicants have found that after approximately one (1) hour the pathogen compartment is fully loaded; after one hour, viral inactivation is not increased upon illumination.

In this embodiment of the method, at this stage in the process, the extra-cellular fluid (plasma protein) has not been separated from the cell component (red blood cells). Certain advantages are achieved by not removing the extra-cellular fluid, prior to adding the photoactive agent. Because the extra-cellular fluid compartment includes lipoproteins it acts as a reservoir station during the process.

In this regard, the ratio of photoactive agent in the red blood cell compartment to the pathogen compartment is critical. With respect to at least some lipophilic photoactive agents, if the plasma protein is washed away prior to adding the photoactive agent, the ratio of photoactive agent within the pathogen compartment to the blood cell compartment may shift in an undesirable fashion.

Ideally, it would be desirable if all of the photoactive agent were included in the pathogen compartment and none in the red cell compartment. By allowing the plasma protein to remain, (initially when the agent is being distributed between the pathogen, blood cell and extracellular compartments), a large portion of the photoactive agent is prevented from entering into the blood cell compartment while still allowing the pathogen compartment to be adequately loaded. The extracellular compartment contains lipids, lipoproteins, and proteins which bind lipophilic photoactive agents in a reversible manner and thereby can serve as carriers for the distribution of the photoactive agents. The net result of having the extracellular lipid/proteins present at the time of addition of many lipophilic photoactive agents is that an adequate loading of the pathogen compartment can be achieved while minimizing the loading of the blood cell compartment.

It has been found that when the plasma proteins are not initially removed and remain when the photoactive agent is added to blood component, after the agent equilibrates with the fluid, approximately 80 to about 90% of the photoactive agent is found in the extra-cellular (protein) compartment and approximately 10 to about 20% in the cellular (red cell) compartment. Therefore, after the plasma proteins are washed out, at most only 20% of the photoactive agent loaded into the blood component remains.

An advantage achieved by removing the plasma protein after the photoactive agent is added, is that excess photoactive agent including that which may be free or bound, can be removed. It is believed that even if the photoactive agent does not bind with a blood component cell membrane, the photoactive agent can cause cell damage. Damage may occur secondary to oxidative damage caused by singlet oxygen or other photochemical events generated by the photoactive agent activation adjacent to, but outside, the cell membrane.

Additionally, it may be desirable to remove the excess photoactive agent to reduce the generation of any photoproducts. By washing out the unbound photoactive agent prior to irradiation, one can reduce the risk of the generation of such photoproducts.

A further advantage of treating the blood component to remove unbound photoactive agents is that it may decrease the light exposure time required to disinfect the product. By removing unbound photoactive agents, one may be able to shorten the light exposure time required to achieve a given microbicidal effect after washing away the unbound photoactive agent. This may be important, with respect to processing large numbers of, for example, red cell units.

As previously noted, if desired, the plasma proteins can be removed prior to the addition of the photoactive agent. Certain advantages may be achieved through this embodiment of the method. For example, with respect to photoactive agents that are hydrophilic, if the blood component is washed after such photoactive agents are added, all or most of the photoactive agent may be washed out. Therefore, with respect to hydrophilic photoactive agents, such as sulfonated aluminum phthalocyanines, the washing step should occur prior to the addition of the photoactive agent.

Additional advantages of this embodiment of the process include the ease of incorporation of the process into a large scale treatment process and that less photoactive agent may be required reducing the costs of the process. Further, if the plasma proteins are removed through washing, the photoactive agent can be present in the solution used to resuspend the cells.

It is also envisioned, that if the plasma proteins are removed prior to adding the photoactive agent a compound can then be added to the fluid or utilized to absorb the excess photoactive agent. Examples of such compounds include activated carbon.

In the treating, or removal step, one attempts to remove substantially all the plasma proteins. Initially the extracellular portion of the blood components could contain greater than 90% by weight plasma. At a minimum the blood component should be treated so that it comprises no more than approximately 5% by weight plasma. Preferably the blood component should be treated so that the total content of the blood component comprises 1% or less by weight plasma, e.g., in the case of red cells.

The body fluid can be treated in a number of ways to reduce the concentration of extracellular component. Examples include filtration, washing, elutriation, and chromatography.

With respect to a blood cell component, as used herein "washing" refers to a process by which the blood component is centrifuged. This results in a pellet and supernatant. The supernatant is then removed and the pellet can be resuspended through the addition of, for example, a buffered saline solution. If desired, a storage solution can be used to resuspend the cells. By using a storage solution, after the irradiation phase of the process the blood component can be stored. However, as set forth in detail below, prior to adding any protein containing substance a predefined period must elapse after irradiation.

If desired, a number of washing steps can be utilized.

During the washing step, a "detergent" can be used to extract excess lipophilic photoactive agents from the blood cell compartment. For example, a lipophilic phospholipid solution can be used to resuspend the cells. Such lipophilic phospholipid solutions include triglycerides (LCTs, MCTs, and SCTs) and fatty acids.

After the washing steps are completed, the product is then irradiated with light having the appropriate wavelength(s). This step can proceed as follows: in the case of red cells treated with a photosensitizer benzoporphyrin derivative, the red cell sample can be exposed to light of a wavelength centered at approximately 690 nm for an appropriate period of time, for example, 30 seconds to six hours.

If desired, after the irradiation step, a further washing step, or other removal step can be performed.

Pursuant to the present invention, after the irradiation step, the blood component, is not combined with additional plasma and/or other protein containing substances either in vivo or in vitro for a predefined period of time. The irradiation of the photoactive agents causes the cellular component, e.g., red cells, to be activated so that they will nonspecifically bind with plasma proteins and become coated with IgG.

As set forth below, it has been found that for cells treated with BPDs after approximately three (3) hours the cellular component, e.g. red blood cells, will not substantially bind with plasma proteins. Accordingly, after a predefined time period, e.g., at least 3 hours and preferably 18 hours, the cells can then be infused into a patient or combined with plasma or other protein containing substances By way of example, and not limitation, examples of the present invention will now be given:

EXAMPLE 1

This example examines the virucidal and immunological consequences of treating red blood cells (RBCs) with benzoporphyrin derivative (BPD) plus washing prior to red light activation on red cell concentrates as a function of BPD dose.

The following materials were used:
1. Petri dish 150 centimeters in diameter.
2. AS-1 human red blood cell concentrate.
3. Physiologic phosphate buffered saline solution (PBS).
4. ARC-8 storage media Lot NR 5203 American Red Cross (Vo Sanguinis 60: 88-98 1991).
5. 150 ml blood storage bag (PL146).
6. BPD 2.02 mg/ml Lot: CB1-91 Quadra Logic Technologies benzoporphyrin derivative (BPD).
7. Vesicular Stomatitis Virus (VSV).

The procedure used was as follows:
1. Approximately 216 ml of blood was spiked with VSV to achieve $1 \times 10^6$ pfu/ml (2.16 ml of $10^8$ VSV in 216 ml AS-1 RBCs) and incubated for 1 hour with agitation prior to the addition of BPD.
2. 31 ml of blood volume was aliquoted into 50 ml centrifuge tube. BPD was added into the tubes directly to achieve a final concentration of 0, 1.0, or 1.5 ug/ml, mixed and allowed to equilibrate with the blood for 1 hour prior to wash.

3. RBCs were washed two times using PBS, centrifuged for 10 min at 2500 × g. The wash volume was 25 ml and the samples were gently vortexed between wash steps to insure good mixing. For the last wash, the cells were resuspended to a total volume of 31 ml using PBS.

4. The blood was exposed in the petri dish in a light box with agitation (irradiation 6.5 Joules/cm$^2$) (GE red lamps fluorescent at 1.8 mW/cm$^2$) for 1 hour.

5. The post-irradiated samples were transferred to 50 ml centrifuge tubes.

6. The tubes were centrifuged for 10 minutes at 2500 × g and the supernatant was discarded. RBCs were washed out with one wash of ARC-8. For the last wash the samples were brought up to a total volume of 31 ml using ARC-8.

7. Samples (3 ml aliquots) for quantitation of viral kill were collected and assayed on the day of irradiation.

8. Samples (2 ml aliquots) for assessing the cell physiology were collected on the days 1, 7, 14, and 28 post-irradiation. Parameters measured were hemoglobin, hematocrit and direct anti-globulin test (DAT). The DAT test was performed according to the conventional method (as described in the American Association for Blood Banks Technical Manual, 10th edition, 1990, editor Richard H. Walker, ISBN 0-915355-75-2 pages 147–157). Prior to performing the DAT test, RBCs were allowed to incubate for greater than 3 hours and then were placed in autologous plasma at 37 dg C for 1 hour.

The tubes were labeled using the following information:

| Code # | | | |
|---|---|---|---|
| A = VSV NO BPD | no wash | no light | no wash |
| B = VSV NO BPD | 2× wash/PBS | no light | 1× wash/ARC-8 |
| C = VSV 1.5 ug/ml BPD | no wash | light | no wash |
| D = VSV 1.0 ug/ml BPD | 2× wash/PBS | light | 1× wash/ARC-8 |
| E = VSV 1.5 ug/ml BPD | 2× wash/PBS | light | 1× wash/ARC-8 |

| Sample Code | Storage Day | Virus TCID$_{50}$ | PL - HGB (mg/dL) | Hemolysis % | DAT Result − = negative + = positive |
|---|---|---|---|---|---|
| A | 1 | >7.25 | 49 | | − |
| B | 1 | 4 | 141 | | − |
| C | 1 | 3 | 45 | | + |
| D | 1 | <2 | 66 | | − |
| E | 1 | <2 | 78 | | − |
| A | 7 | | 111 | 0.33 | |
| B | 7 | | 168 | 0.30 | |
| C | 7 | | 154 | 0.31 | |
| D | 7 | | 106 | 0.34 | |
| E | 7 | | 108 | 0.40 | |
| A | 14 | | 125 | 0.39 | |
| B | 14 | | 137 | 0.28 | |
| C | 14 | | 395 | 0.71 | |
| D | 14 | | 120 | 0.48 | |
| E | 14 | | 117 | 0.46 | |
| A | 28 | | 186 | 0.50 | |
| B | 28 | | 204 | 0.43 | |
| C | 28 | | 1650 | 2.23 | |
| D | 28 | | 195 | 0.65 | |
| E | 28 | | 284 | 0.98 | |

Virus TCID$_{50}$ represents the tissue culture infectious dose per ml of red cells for each sample on a log scale. For example, a value of 3 indicates 1,000 infective virus per ml and a value of <2 means less than 100 infective virus per ml.

The indicator cells for the VSV assay were Vero cells grown in 96 well microtiter plates. The assay methods employed basic virology techniques as summarized in Virology, Wolfgang K. Joklik, second edition, "The Nature, Isolation, and Measurement of Animal Viruses," page 10, 1985. PL-HGB represents the supernatant hemoglobin values from the stored blood samples. HCT represents the hematocrit of the stored blood samples. % Hemolysis represents the percentage of red cells have been lysed.

DAT results are either positive (+) or negative (−) based upon agglutination of RBCs with a rabbit anti-human IgG antibody. A positive result is demonstration of the RBCs being coated with human IgG.

The results of this experiment demonstrate that the wash method of the present invention (Samples D, E) results in greater vital reduction than in the non-wash method (Sample C) even when lower concentrations of BPD are employed. The cells treated with the wash method have better cell physiology characteristics: less hemolysis upon storage and negative DAT results after being challenged with plasma.

EXAMPLE 2

The goal of this study was to compare the virucidal and immunological consequences of treating RBCs with benzoporphyrin derivative (BPD) using both a nonwash method and a wash method as a function of light exposure time.

The materials used were the same as in Example 1.

The procedure below was followed to generate the following Samples A–F:

The tubes were labeled using the following information:

| Code # | | | |
|---|---|---|---|
| A = VSV no BPD | no wash | no light | no wash |
| B = VSV no BPD | no wash | no light | 1× wash/ ARC-8 |
| C = VSV no BPD | no wash | light | no wash |
| D = VSV no BPD | 2× wash/PBS | light | 1× wash/ ARC-8 |
| E = VSV 1.0 ug/ml BPD | no wash | light | no wash |
| F = VSV 1.0 ug/ml BPD | 2× wash/PBS | light | 1× wash/ ARC-8 |

1. Approximately 256 ml of blood was spiked with VSV to achieve 1×10*6 pfu/ml (2.56 ml of 10*8 VSV in 216 ml AS-1 RBCs) and incubated for 1 hour with agitation prior to added BPD.

2. 31 ml of blood volume was added into 50 ml centrifuge tubes. BPD was added into the tubes directly to achieve a final concentration of 1.0 ug/ml, mixed and allowed to equilibrate with the blood for 1 hour prior to the next step.

3. For the nonwash method (Sample E), the blood was exposed in the petri dish in light box with agitation (GE red lamps at 1.8 mW/$cm^2$) and agitated with a horizontal shaker (100 rpm).

4. a) For the wash method (Sample F), RBCs were washed two times with PBS, and centrifuged for 10 min. at 2500 × g. The wash volume was 25 ml and the samples were gently vortexed between wash steps to insure good mixing. After the last wash with PBS, the samples were brought to a total volume of 31 ml.

b) The blood was exposed in the petri dish in a light box with agitation as described in Step No. 3 above.

5. For both methods, samples (1 ml aliquots) were collected for quantitation of viral killing at 15, 30, 45, and 60 minutes. Samples were assayed on the day of irradiation.

6. The post-irradiated samples were transferred to 50 ml centrifuge tubes.

7. The tubes were centrifuged for 10 min. at 3000 rpm and the supernatants were discarded. Samples B and F RBCs were washed once with ARC-8. After the last wash, the samples were brought to a total volume of 27 ml using ARC-8.

8. Samples (3 ml aliquots) for assessing the cell physiology were collected on the days 1, 7, 14, and 28 post-irradiation. Parameters measured were hemoglobin, hematocrit, and DAT status.

Sample

| Code | Sample Description |
|------|--------------------|
| A | VSV no BPD no wash no light |
| B | VSV no wash no light 1× wash/ARC-8 |
| C | VSV no BPD no wash light |
| D | VSV no BPD 2× wash/PBS light 1× wash/ARC-8 |
| E | VSV, 1.0 ug/ml BPD, no wash, light, no wash |
| F | VSV, 1.0 ug/ml BPD, 2× wash/PBS, light, 1× wash/ARC-8 |

| Code | Storage Day | Virus TCID$_{50}$ after 60 minutes light exposure | PL-HGB (mg/dL) | Hemolysis % | DAT Result |
|------|----|------|-----|------|----|
| A | 1 | 7.25 | 25 | 0.07 | — |
| B | 1 | 6.7 | 53 | 0.10 | — |
| C | 1 | 7.25 | 61 | 0.18 | — |
| D | 1 | 5.85 | 175 | 0.21 | — |
| E | 1 | 4.8 | 70 | 0.20 | + |
| F | 1 | <2.0 | 71 | 0.15 | — |
| A | 7 |  | 78 | 0.23 |  |
| B | 7 |  | 61 | 0.11 |  |
| C | 7 |  | 76 | 0.21 |  |
| D | 7 |  | 173 | 0.24 |  |
| E | 7 |  | 87 | 0.22 |  |
| F | 7 |  | 83 | 0.26 |  |
| A | 14 |  | 86 | 0.25 |  |
| B | 14 |  | 96 | 0.18 |  |
| C | 14 |  | 90 | 0.26 |  |
| D | 14 |  | 174 | 0.26 |  |
| E | 14 |  | 156 | 0.40 |  |
| F | 14 |  | 136 | 0.42 |  |
| A | 28 |  | 116 | 0.33 |  |
| B | 28 |  | 108 | 0.23 |  |
| C | 28 |  | 93 | 0.26 |  |
| D | 28 |  | 54 | 0.06 |  |
| E | 28 |  | 350 | 0.64 |  |
| F | 28 |  | 215 | 0.73 |  |
| A | 35 |  | 212 | 0.62 |  |
| B | 35 |  | 69 | 0.20 |  |
| C | 35 |  | 90 | 0.25 |  |
| D | 35 |  | 123 | 0.20 |  |
| E | 35 |  | 233 | 0.46 |  |
| F | 35 |  | 195 | 0.62 |  |

Figure 2:
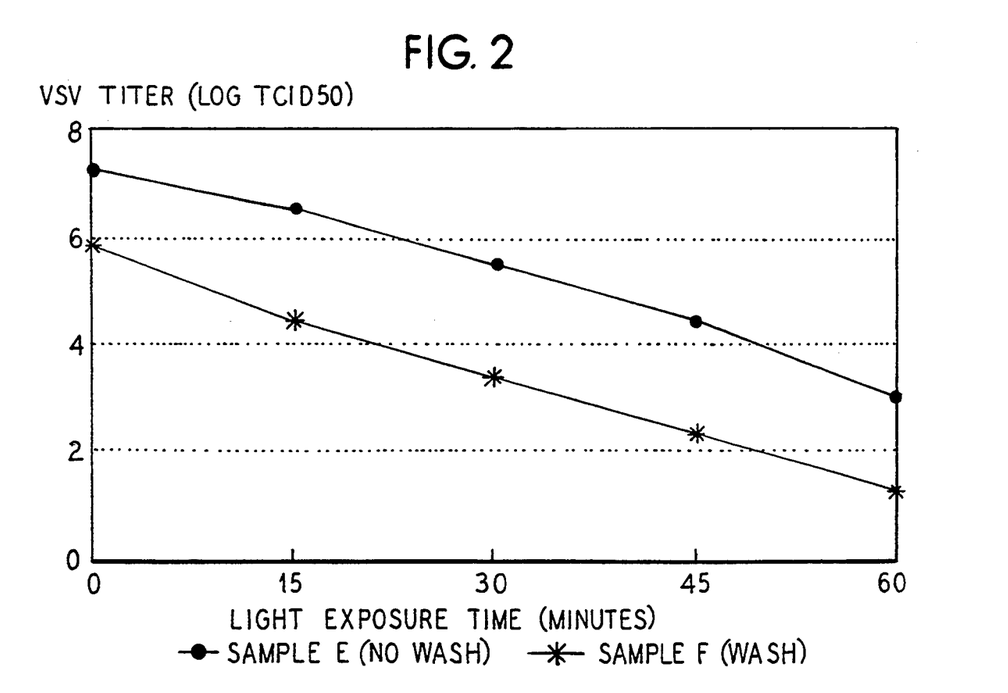
FIG. 2 illustrates graphically BPD inactivation of VSV as a function of light dose using a no wash and wash process.

FIG. 2 illustrates graphically BPD inactivation of VSV as a function of light dose using nonwash and wash methods. The BPD dose is 1.0 ug/ml for both samples.

Results of the experiments demonstrate that the rate of viral killing was the same for nonwash and wash method and a greater overall reduction in virus for the wash method than the nonwash method. This demonstrates that removal of unbound BPD did not diminish the viricidal effect of the treatment. As in Example 1, the wash method resulted in less hemolysis and negative DAT red blood cells.

EXAMPLE 3

The following examples also illustrate differences between the viral inactivation process for red cell concentrates treated in the presence or absence of limited amounts of plasma.

Red cell concentrates (RCC) were prepared from whole blood and spiked with a specific amount of virus (Vesicular Stomatitis Virus or VSV) in a manner similar to the protocol described in Example 1. For the plasma limitation method, samples were washed prior to light exposure. These examples evaluate the following parameters: vesicular stomatitis virus (VSV) (VSV used as a model virus in these studies) inactivation/depletion and DAT results.

BPD STUDY

Comparison of results from viral inactivation studies using the following two procedures:
a) no plasma limitation method;
b) plasma limitation method.

TABLE 1

| NO PLASMA LIMITATION METHOD (Approximately 14% plasma present) | | | |
|---|---|---|---|
| Experiment # | BPD (µg/ml) | Viral Depletion (logs) | % Hemolysis (on storage day) | DAT |
| 1 | 1.0 | 4-6 |  | Positive |
|   | 1.5 | >6 |  | Positive |

TABLE 2

| PLASMA LIMITATION METHOD | | | |
|---|---|---|---|
| Experiment # | BPD (µg/ml) | Viral Depletion (logs) | % Hemolysis (on storage day) | DAT |
| 1 | 1.0 | >6 |  | negative |
|   | 1.5 | >6 |  | negative |
| 2 | 0.75 | >6 |  | negative |
|   | 1.0 | >6 |  |  |

For the results shown in Tables 3 and 4, the following procedure was followed:

For Table 3, 21 ml packed red cells were washed three times in PBS (total volume 50 ml) followed by one wash (50 ml total volume) in ARC-8 (red cell storage solution). Aliquots were prepared from the washed RC as follows: >10$^6$ pfu VSV/ml was added to RC. 2%, 3%, or 5% plasma was added to RC in ARC-8 (4 sample groups).

Aliquots of each sample group were treated with BPD (0, 0.25, 0.5, or 0.75 µg/ml) for one hour followed by exposure to red light (light box similar to that described in Example 1) for one hour. Samples were assayed for VSV inactivation (plaque assay) and DAT status was determined visually immediately following treatment and after plasma challenge. Plasma challenge involved storage of treated RCC for approximately 18 hours (overnight) at 4° C. followed by addition of 100% plasma for one hour at 37° C.

It should be noted that the initial washing of red cells was performed only to ensure that addition of amounts of plasma indicated resulted in the concentrations specified.

TABLE 3

| | DAT (+/−) | | VSV |
|---|---|---|---|
| | Pre* | Post* | Inactivation |
| RCC + 2% Plasma | | | |
| Light Only | − | − | (input 7.0 logs) |
| 0.25 μg/ml | − | − | 3.2 logs |
| 0.5 μg/ml | − | − | 7.0 logs |
| 0.75 μg/ml | − | − | 7.0 logs |
| RCC + 3% Plasma | | | |
| Light Only | − | − | (input 6.9 logs) |
| 0.25 μg/ml | − | − | 2.6 logs |
| 0.5 μg/ml | − | − | 6.3 logs |
| 0.75 μg/ml | − | − | 6.9 logs |
| RCC + 5% Plasma | | | |
| Light Only | + | + | (input 7.2 logs) |
| 0.25 μg/ml | + | + | 3.1 logs |
| 0.5 μg/ml | + | + | 5.8 logs |
| 0.75 μg/ml | + | + | 2.2 logs |

*Pre = Preplasma Challenge
*Post = Post Plasma Challenge

The results set forth in Table 4 below are for studies performed in a similar manner to those used to generate Table 3.

TABLE 4

| | DAT (+/−) | | VSV |
|---|---|---|---|
| | Pre* | Post* | Inactivation |
| RCC, 4.7% Plasma HT 58% | | | |
| Light Only | − | − | (input 7.3 logs) |
| 0.25 μg/ml BPD | − | − | 2.2 logs |
| 0.5 μg/ml BPD | − | − | 4.9 logs |
| 0.75 μg/ml BPD | − | − | 6.0 logs |
| RCC, 5.9% Plasma HT 56% | | | |
| Light Only | − | − | (input 7.3 logs) |
| 0.5 μg/ml BPD | − | − | 3.9 logs |
| 0.75 μg/ml BPD | − | − | 5.5 logs |
| 1.0 μg/ml BPD | − | − | 7.0 logs |
| RCC, 6.7% Plasma HT 62% | | | |
| Light Only | − | ND | (input 7.4 logs) |
| 0.5 μg/ml BPD | − | ND | 4.5 logs |
| 0.75 μg/ml BPD | − | ND | 6.9 logs |
| 1.0 μg/ml BPD | + | ND | 7.4 logs |

*Pre  Pre Plasma Challenge
*Post  Post Plasma Challenge
ND  Not Determined

Table 3 and Table 4 demonstrate that in order to eliminate DAT positivity, it is necessary to perform the viral inactivation procedure in the presence of limited (approximately 5% or less) amounts of plasma.

The data, as well as the data set forth in Example 4, also refutes the Wagner et al publication referred to previously, in that the inventors have shown that it is possible to prevent a positive DAT score (significant levels of IgG binding to red cell surface) in red cells that have been treated by a plasma limitation method as long as the treated blood component is not exposed to plasma proteins for a defined period following light exposure. In the case of BPD, this period has been shown to be 3 hours (minimum) and preferably 18 hours.

Other Photosensitizers

Treatment of RCC was carried out using both the Plasma Limitation Method and No Plasma Limitation Method to assess DAT status of RC following treatment with a variety of photosensitizer and light. White light was utilized in studies with photofrin and merocyanine 540; red light was utilized with aluminum phthalocyanine. Doses of each photosensitizer examined are shown in the table below.

TABLE 5

| | | DAT SCORE | |
|---|---|---|---|
| PHOTO-SENSITIZER | DOSE (μg/ml) | No Plasma Limitation | Plasma Limitation |
| Photofrin | 0 (light only) | − | − |
| | 5 | + | − |
| | 10 | + | − |
| | 20 | + | − |
| | 20 (no light) | − | − |
| Tetrasulfonated Aluminum Phthalocyanine | 0 (light only) | − | − |
| | 4.7 (5 μM) | + | − |
| | 9.4 (10 μM) | + | − |
| | 18.8 (20 μM) | + | − |
| Merocyanine | 10 | + | − |

EXAMPLE 4

The following experiment demonstrate, using flow cytometry, that red cells treated by a plasma limitation method with BPD and light, do not have any significant affinity for binding IgG if challenged (by plasma addition) at 3 hours following light exposure.

The treatment protocol was as follows:

Red cell concentrate (RCC) was prepared from whole blood (RCC with approximately 14% plasma in Adsol).

20 ml RCC was centrifuged at 2000 rpm for 10 minutes.

The supernatant (plasma/Adsol) was removed.

The resultant pellet (RC) was resuspended to 50 ml with Adsol and then centrifuged at 2000 rpm for 10 minutes.

The supernatant was removed and RC resuspended to 20 ml with adsol.

BPD was added to samples as follows: 0, 0.5, 0.75, 1.0 ug BPD/ml.

The sample was incubated for 1 hour in the dark, and exposed to red light (light box) for 1 hour.

The cells were left in the dark at room temperature for 3 hours.

Autologous plasma was added to samples to give plasma in Adsol. The samples were stored at 4° C. overnight.

Flow cytometry was performed.

Preparation of red cells for Flow Cytometry was as follows:

1. Dilute RCC 1/10 in PBS.
2. Add 50 ul of diluted RCC to a 12×75 mm snap cap tube.
3. Add approximately 3 ml of PBS.
4. Centrifuge for 2 min. at approximately 3000 rpm.
5. Aspirate supernatant.
6. Mix the cells in the remaining PBS by gently flicking the tube.
7. Add approximately 3 ml of PBS (2nd wash).
8. Centrifuge as before.
9. Aspirate the supernatant.
10. Mix the cells in the remaining drop of PBS by gently flicking the tube.
11. Add 400 ul of 1/100 of 1'Ab.
12. Incubate at 4° C. for 30–40 min., shaking the tube occasionally.
13. Add PBS and wash 2× as before.
14. Add 400 ul of 2'Ab.
15. Incubate in the dark for 30–40 min., shaking the tubes occasionally.

16. Wash the cells 2× with PBS as before.
17. Resuspend cell pellet in 600 ul of 1% paraformaldehyde in BPS.
18. Store samples in the dark at 4° C. until analyzed using flow cytometry, samples can be stored up to 3 days.

The following reagents were used:
1'Ab: Rabbit anti Human IgG (Serotec ordered from Cedarlane, cat # STAR 33).
2'Ab: Goat F(ab) anti Rabbit IgG (whole molecule) FITC ordered from Cappel, cat # 55658.
1% paraformaldehyde in PBS (w/v): Heat until 70° C. to dissolve, do not boil. When cooled adjust pH to 7.4. Keep in the dark at 4° C., shelf life 6 months.

The following table illustrates the results from flow cytometric analysis of treated RC which were labeled with antisera to determine the presence of IgG on their surface.

Figure 3A:
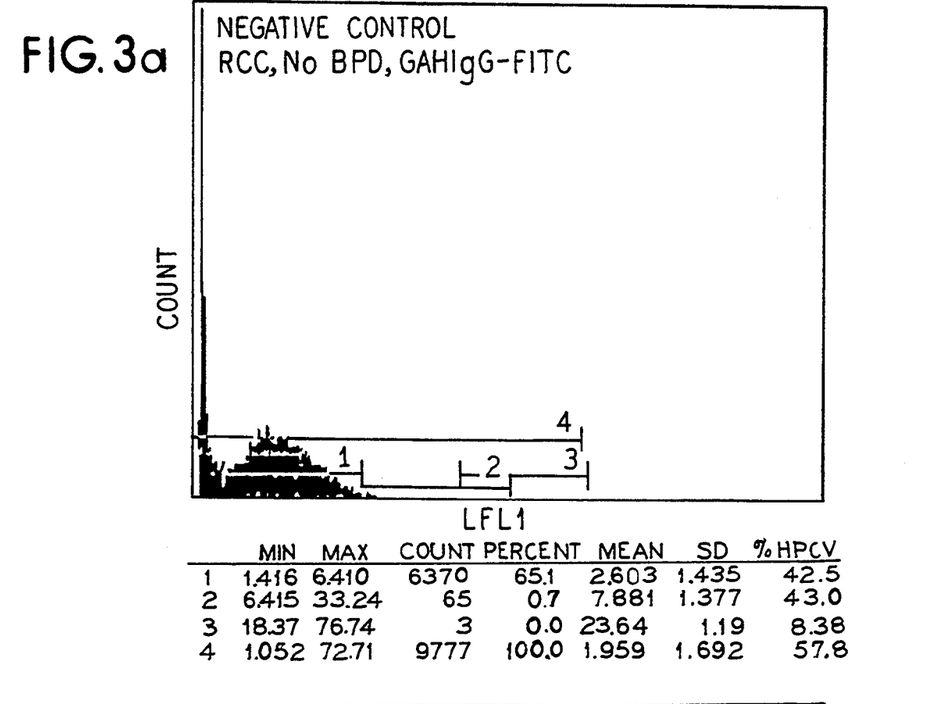
FIGS. 3a-3c are graphs of flow cytometric analysis of IgG binding to red blood cells.
Figure 3B:
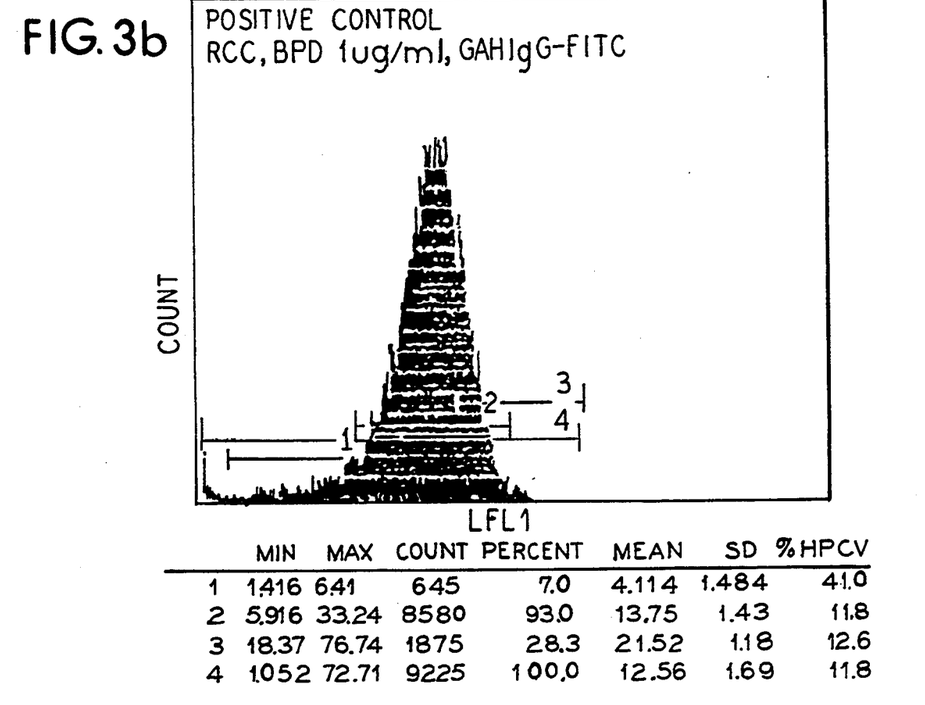
Figure 3C:
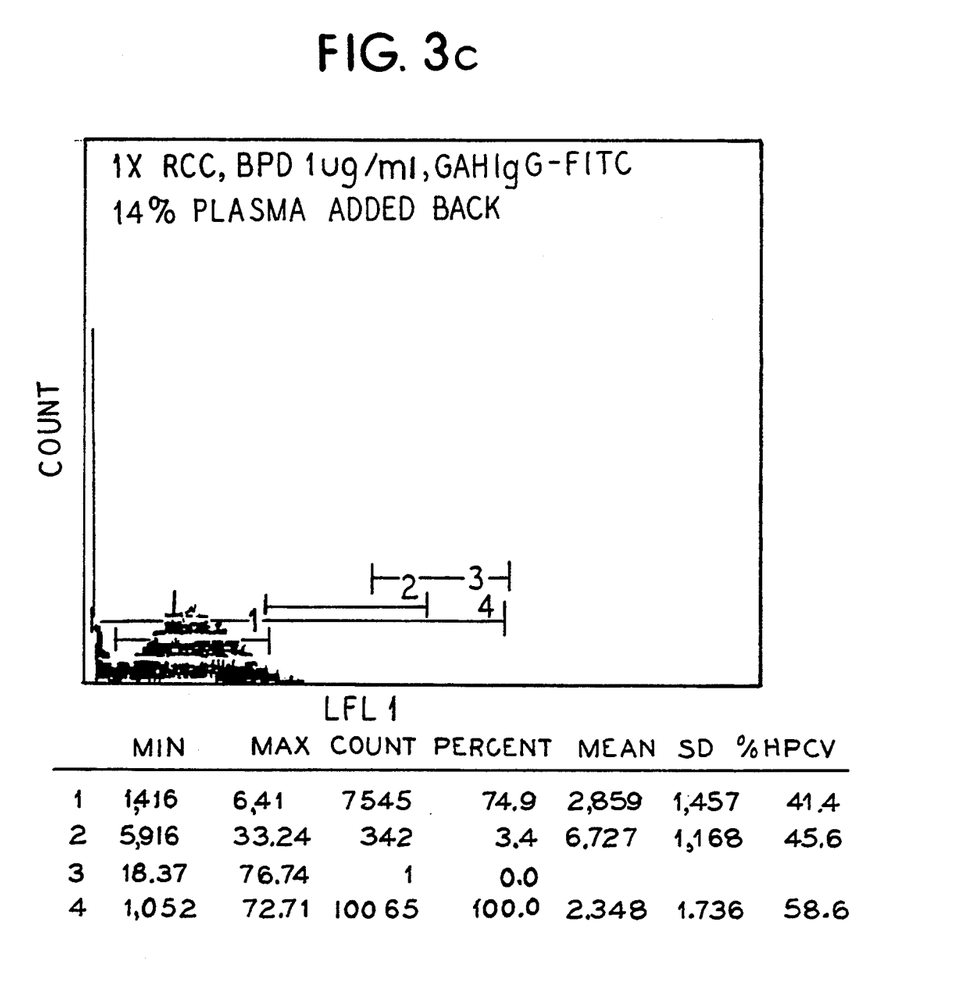

Cells contained in AREA 1 are considered negative for IgG binding. Cells contained in AREA 2 are considered positive. FIGS. 3a–3c set forth representative graphs.

| BPD Dose | Percent* Cells Contained in: | | | |
|---|---|---|---|---|
| | AREA 1 (NEGATIVE) | | AREA 2 (POSITIVE) | |
| (ug/ml) | Pre** | Post*** | Pre** | Post*** |
| 0 | 67 | 66 | 1 | 1 |
| 0.5 | 71 | 70 | 2 | 2 |
| 0.75 | 73 | 72 | 3 | 2 |
| 1.0 | 76 | 75 | 3 | 3 |

*Note that representative graphs, FIGS. 3a—3c, illustrate total numbers of cells as 100%. The cells not accounted for in Areas 1 and 2 are contained in the total cell population, Area 4. For the table above, the remaining cells are all less fluorescent (more negative) than the population contained in Area 1.
In the Figures, red cell concentrate (RCC) = 14% plasma, 55% HCT, washed 1× red cell concentrate (1× RCC), and no wash, supernatant removed = no wash RCC.
**Pre: Pre-Plasma Challenge
***Post: Post-Plasma Challenge

EXAMPLE 5

In another experiment, performed in a similar manner to Example 4, 1.0 μg BPD/ml was used to treat RCC that had been washed once in Adsol and resuspended in Adsol. Following light exposure, 14% autologous plasma was added after a 3 hour waiting period.

RC were then treated in the following ways: either: left at 4° C. overnight, see (1); or left at 4° C. overnight by heating to 37° C. for 1 hour, see (2); or left for another hour at room temperature in 14% plasma, then heated for 1 hour at 37° C., then stored at 4° C. overnight, see (3). Flow cytometry was then carried out on all samples.

Results from flow cytometry were as follows:

| BPD Dose | Percent Cells Contained in: | |
|---|---|---|
| (ug/ml) | AREA 1 (NEGATIVE) | AREA 2 (POSITIVE) |
| ¹0 | 72 | 5 |
| 1 | 82 | 4 |
| ²*0 | 72 | 0 |
| *1 | 83 | 3 |
| ³0 | 75 | 2 |
| 1 | 86 | 4 |

Figure 4A:
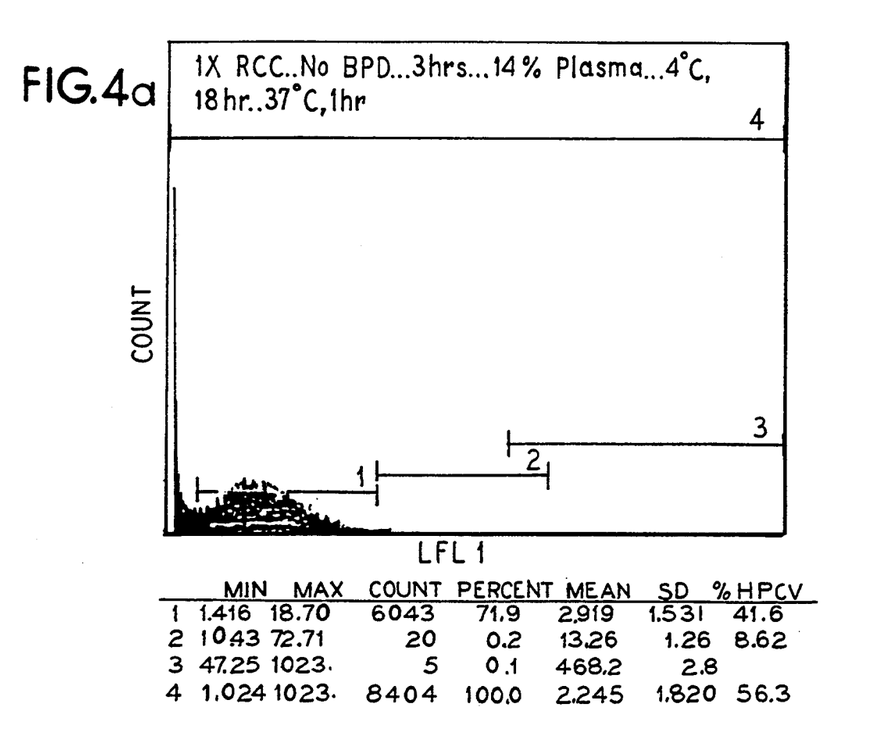
FIGS. 4a-4b are graphs of flow cytometric analysis of IgG binding to red blood cells.
Figure 4B:
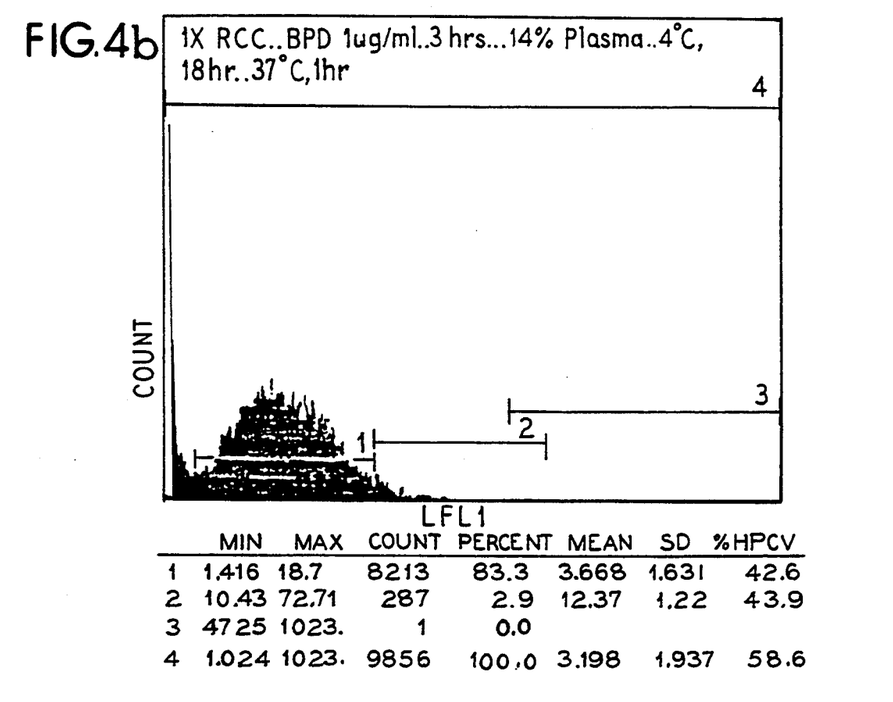

*Illustrated on graphs set forth as FIGS. 4a—4b.

These results demonstrate that there is no significant difference from controls in terms of IgG binding to RC (i.e., they are negative for IgG binding) if one waits for 3 hours prior to challenge with plasma, even when the cells are challenged at 37° C., simulating an in vivo situation.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for destroying viral pathogens in a blood component containing red blood cells and plasma proteins using a photoactive agent comprising the steps of:
   adding a photoactive agent to the blood component;
   treating the blood component to reduce the plasma proteins;
   irradiating the resultant blood component with light of an appropriate wavelength to activate the photoactive agent and thereby inactivate viral pathogens;
   preventing the resultant blood component from contacting plasma proteins either in vivo or in vitro for a period at least approximately three hours in order to prevent the blood component from exhibiting a positive direct antiglobulin test; and
   after the period sufficient, contacting the blood component with plasma proteins either in vivo or in vitro.

2. The method of claim 1 wherein the photoactive agent is chosen from the group consisting of porphyrins, merocyanines, phthalocyanines, pyrrolic macrocycles, psoralens, and photoactive dye stuffs.

3. The method of claim 1 wherein the plasma proteins are reduced prior to the addition of the photoactive agent.

4. The method of claim 1 wherein the plasma proteins are reduced after the addition of the photoactive agent.

5. The method of claim 1 wherein the plasma is reduced so that it comprise no more than approximately 5% by weight of the blood component.

6. The method of claim 1 wherein the treating step includes washing the blood component.

7. The method of claim 1 including a plurality of washing steps.

8. The method of claim 1 wherein the resultant blood component is prevented from contacting additional plasma proteins for at least approximately 18 hours.

9. A method for inactivating viral pathogens in a body fluid that includes red blood cells and extracellular fluid containing plasma proteins comprising the steps of:
   adding a lipophilic membrane binding photoactive agent to a collected body fluid that includes red blood cells;
   treating the body fluid that includes red blood cells to reduce unbound photoactive agent and extracellular fluid proteins; and
   irradiating with an appropriate light the resultant body fluid that includes red blood cells to activate the photoactive agent and thereby inactivate the viral pathogens in the resultant body fluid.

10. The method of claim 9 wherein the body fluid is blood.

11. The method of claim 9 wherein the photoactive agent is chosen from the group consisting of porphyrins, merocyanines, phthalocyanines, pyrrolic macrocycles, and photoactive dye stuffs.

12. The method of claim 9 wherein the body fluid includes an in vitro cell culture.

13. The method of claim 9 wherein the body fluid includes bone marrow.

14. The method of claim 9 wherein the irradiated resultant body fluid is washed.

15. The method of claim 9 wherein extracellular fluid is reduced so that it comprises not more than 5% by weight volume of the body fluid.

16. A method for inactivating viral pathogens in a blood component containing red blood cells and plasma comprising the steps of:
    adding a lipophilic membrane binding photoactive agent to the blood component;
    treating the blood component to reduce unbound photoactive agent and to reduce the plasma to approximately 5% or less of the total weight of the blood component; and
    irradiating a resultant blood component with light of an appropriate wavelength to activate the photoactive agent and thereby inactivate viral pathogens.

17. The method of claim 16 wherein the photoactive drug is chosen from the group consisting of porphyrins, merocyanines, phthalocyanines, pyrrolic macrocycles, psoralens, and photoactive dye stuffs.

18. The method of claim 16 including the step of allowing the photoactive agent to equilibrate with the blood component prior to treating the blood component.

19. The method of claim 18 wherein the step of allowing the photoactive agent to equilibrate has a duration of approximately 5 minutes to 6 hours.

20. The method of claim 18 wherein the step of allowing the photoactive agent to equilibrate has a duration of at least one hour.

21. The method of claim 18 wherein the treating step includes:
    centrifuging the blood component to form a pellet;
    removing the pellet; and
    resuspending the pellet.

22. The method of claim 16 wherein the treating step includes a plurality of washing steps.

23. The method of claim 16 including the step of adding to the resultant blood component a composition including plasma proteins after waiting at least 3 hours.

24. The method of claim 16 including the step of infusing the resultant blood component into a patient after a 3 hour period.

25. The method of claim 16 wherein the lipophilic photoactive drug is a benzoporphyrin derivative.

26. The method of claim 16 wherein the treating step includes the step of adding to the blood component a lipophilic phospholipid reagent.

27. The method of claim 16 comprising a plurality of washing steps.

28. The method of claim 16 wherein the treating step reduces the plasma proteins to approximately 1% or less by weight of the total blood component.

29. The method of claim 16 including the step of washing an irradiated resultant blood component.

30. The method of claim 16 including the step of utilizing a compound to absorb excess photoactive agent.

31. A method for inactivating a virus in a composition comprising red blood cells and plasma comprising the steps of:
    adding a lipophilic membrane-binding photoactive agent to the composition;
    washing the composition to remove unbound photoactive agent and to reduce the plasma to approximately 5% or less by weight of the composition;
    irradiating the composition with light of a wavelength sufficient to activate the photoactive agent in order to inactivate the virus; and
    preventing the irradiated composition from contacting a second composition comprising a plasma protein for a time period of at least approximately 3 hours.

32. The method of claim 31 wherein the photoactive agent is a porphyrin.

33. A method for inactivating a virus in a composition comprising red blood cells and plasma comprising the steps of:
    washing the composition to reduce the concentration of plasma to approximately 5% or less by weight of the composition;
    adding a membrane binding photoactive agent to the composition;
    irradiating the composition with light of a wavelength sufficient to activate the photoactive agent in order to inactivate the virus; and
    adding a second composition comprising a plasma protein after a time period of at least 3 hours.

34. The method of claim 33 wherein the photoactive agent is hydrophilic.

* * * * *